(12) United States Patent
Chambers et al.

(10) Patent No.: US 9,114,259 B2
(45) Date of Patent: Aug. 25, 2015

(54) RECORDING AND RETRIEVAL OF SOUND DATA IN A HEARING PROSTHESIS

(71) Applicant: Cochlear Limited, Macquarie University, NSW (AU)

(72) Inventors: John Chambers, Mona Vale (AU); Michael Goorevich, Naremburn (AU); Konstadinos Hatzianestis, Lane Cove (AU); Koen Van den Heuvel, Hove (BE); Paul M. Carter, West Pennant Hills (AU)

(73) Assignee: Cochlear Limited, Macquarie University (AU)

( * ) Notice: Subject to any disclaimer, the term of this patent is extended or adjusted under 35 U.S.C. 154(b) by 0 days.

(21) Appl. No.: 14/108,760

(22) Filed: Dec. 17, 2013

(65) Prior Publication Data

US 2014/0180362 A1 Jun. 26, 2014

Related U.S. Application Data

(62) Division of application No. 13/461,182, filed on May 1, 2012, now abandoned, which is a division of application No. 11/402,836, filed on Apr. 13, 2006, now Pat. No. 8,170,677.

(30) Foreign Application Priority Data

Apr. 13, 2005 (AU) .............................. 2005901833
Feb. 28, 2006 (AU) .............................. 2006900982

(51) Int. Cl.
*A61N 1/36* (2006.01)
*H04R 25/00* (2006.01)

(52) U.S. Cl.
CPC .......... *A61N 1/36032* (2013.01); *H04R 25/353* (2013.01); *H04R 2225/43* (2013.01); *H04R 2225/67* (2013.01)

(58) Field of Classification Search
CPC ........................ A61N 1/36032; A61N 1/0541
USPC ....................................... 607/55–56, 136–137
See application file for complete search history.

(56) References Cited

U.S. PATENT DOCUMENTS 4,390,756 A * 6/1983 Hoffmann et al. .............. 607/56

* cited by examiner

*Primary Examiner* — Carl H Layno
*Assistant Examiner* — Paula J Stice
(74) *Attorney, Agent, or Firm* — McDonnell Boehnen Hulbert & Berghoff LLP

(57) ABSTRACT

A hearing prosthesis for delivering stimuli to a hearing-impaired recipient is disclosed, the hearing prosthesis comprising: a sound transducer for converting received sound signals into electric audio signals; a sound processor for converting said electric audio signals into stimuli signals; a stimulator for delivering said stimuli to the recipient; a memory for storing data representative of sound signals; and a controller configured to cause selected sound data to be retrieved from said memory and processed by said sound processor.

13 Claims, 17 Drawing Sheets

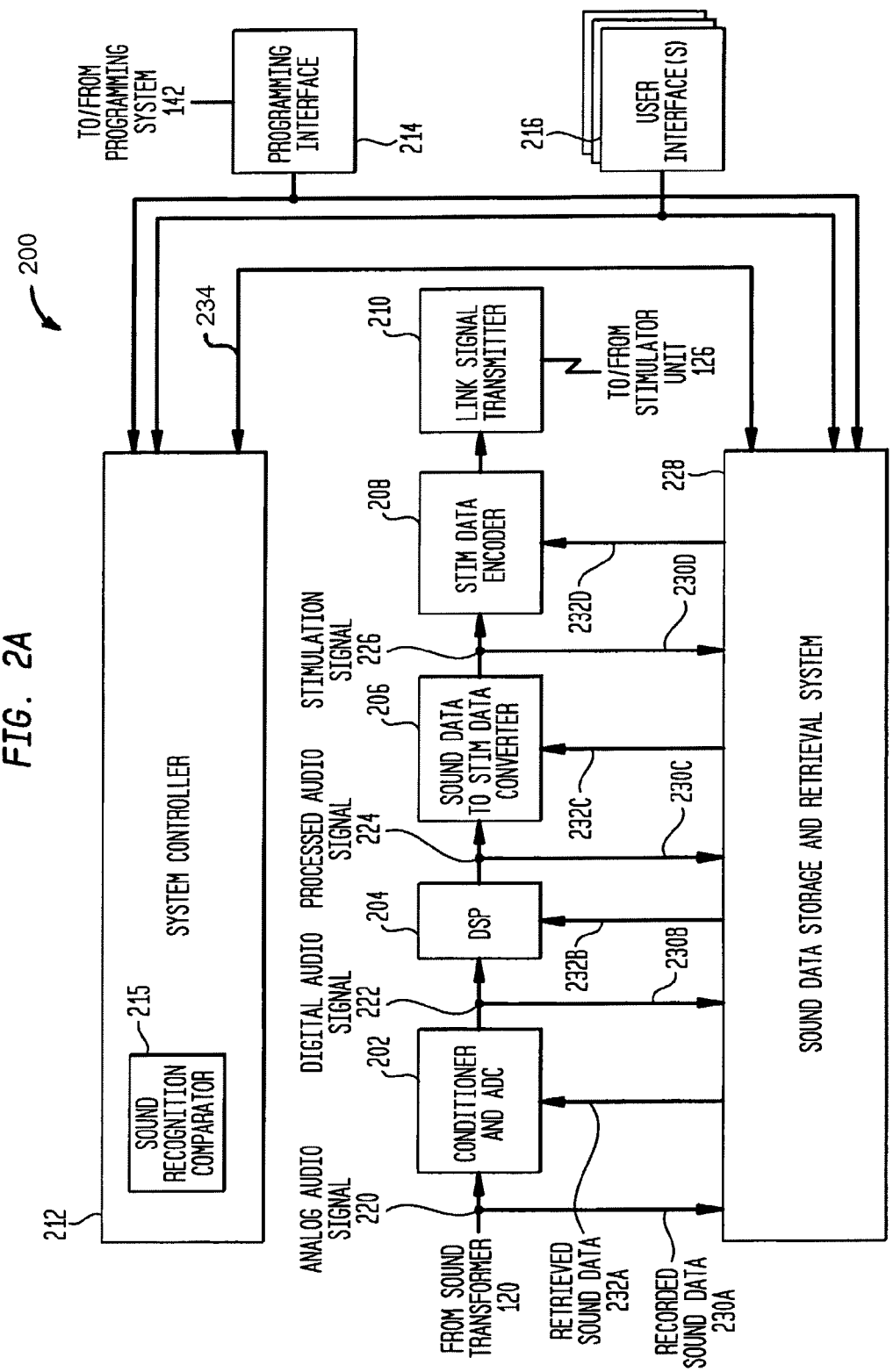

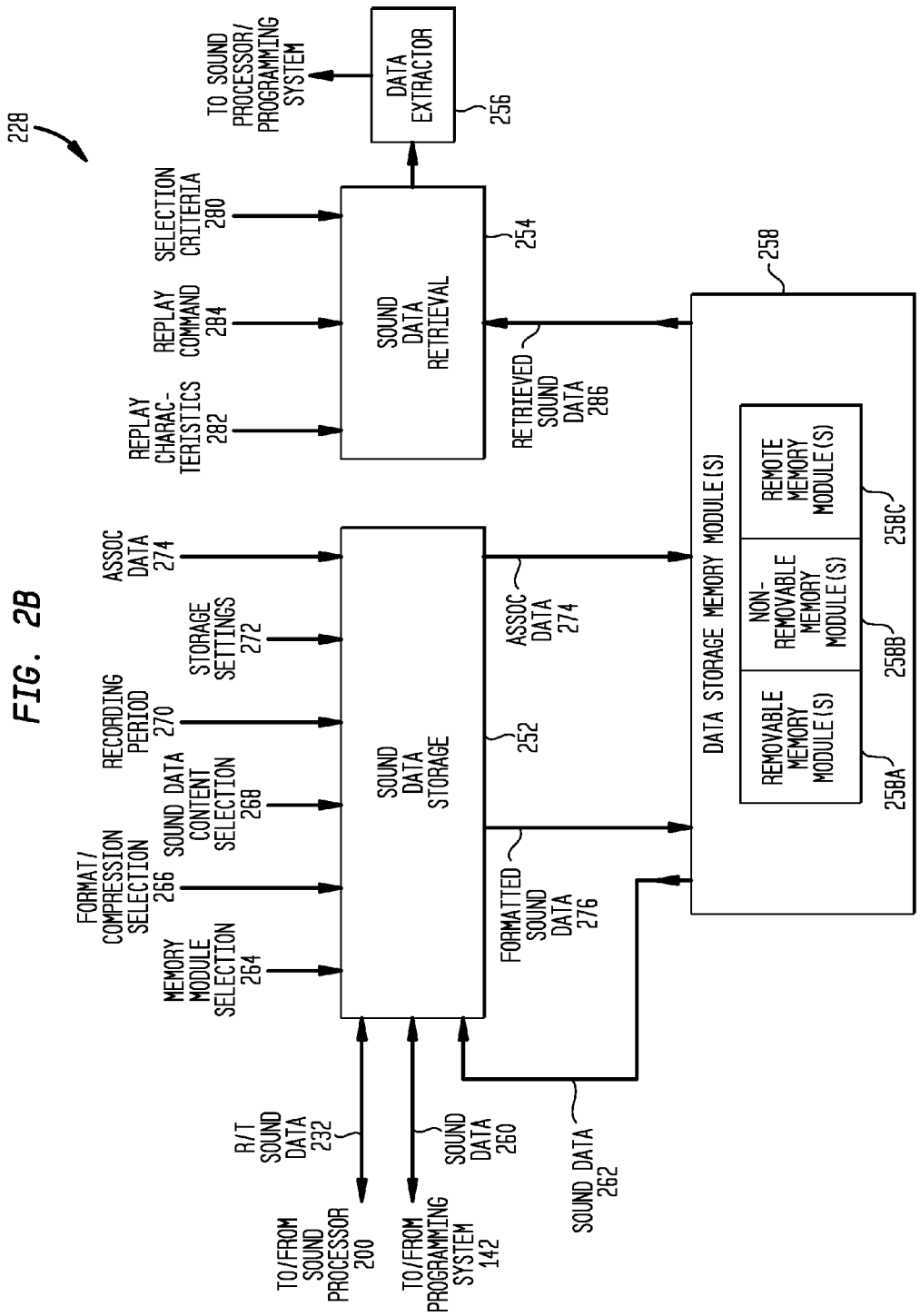

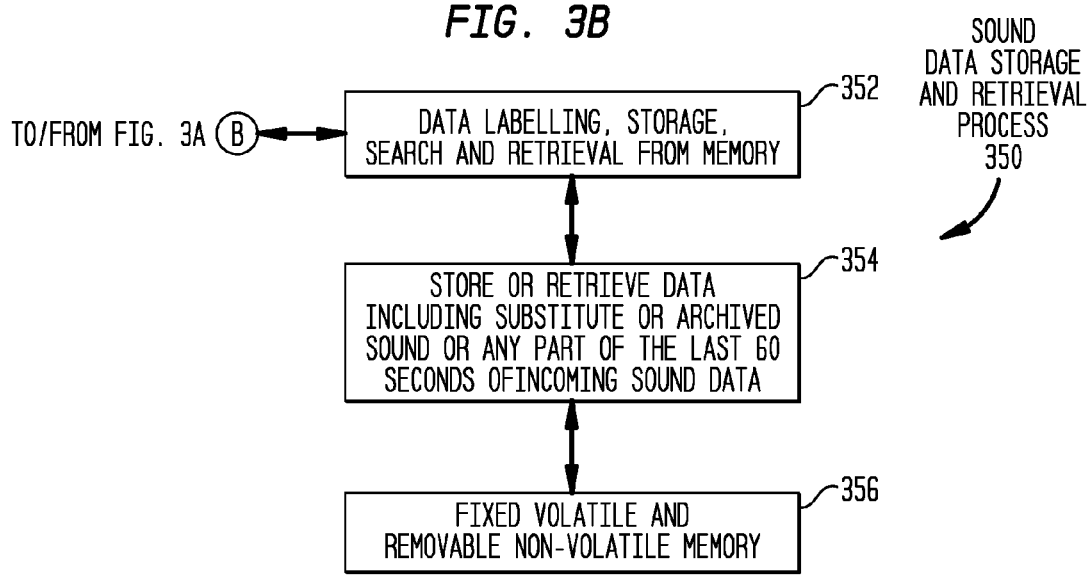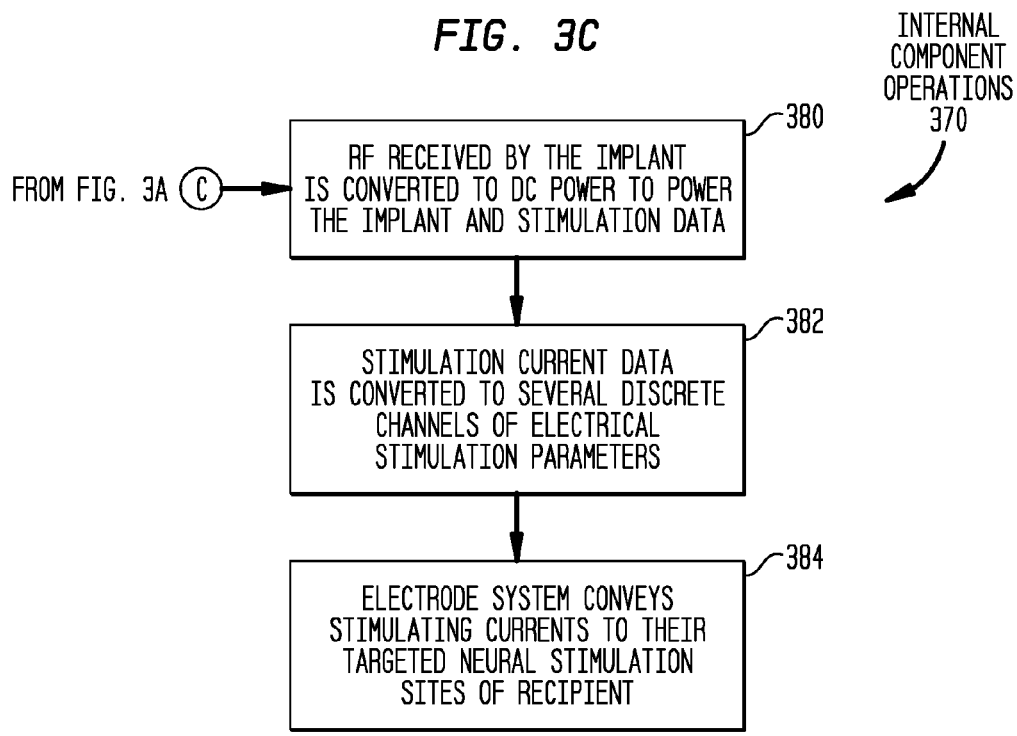

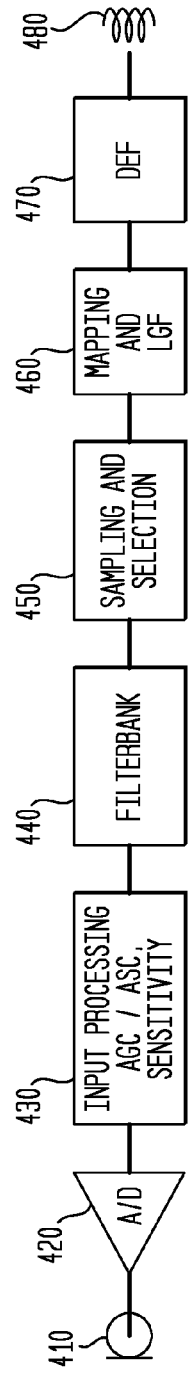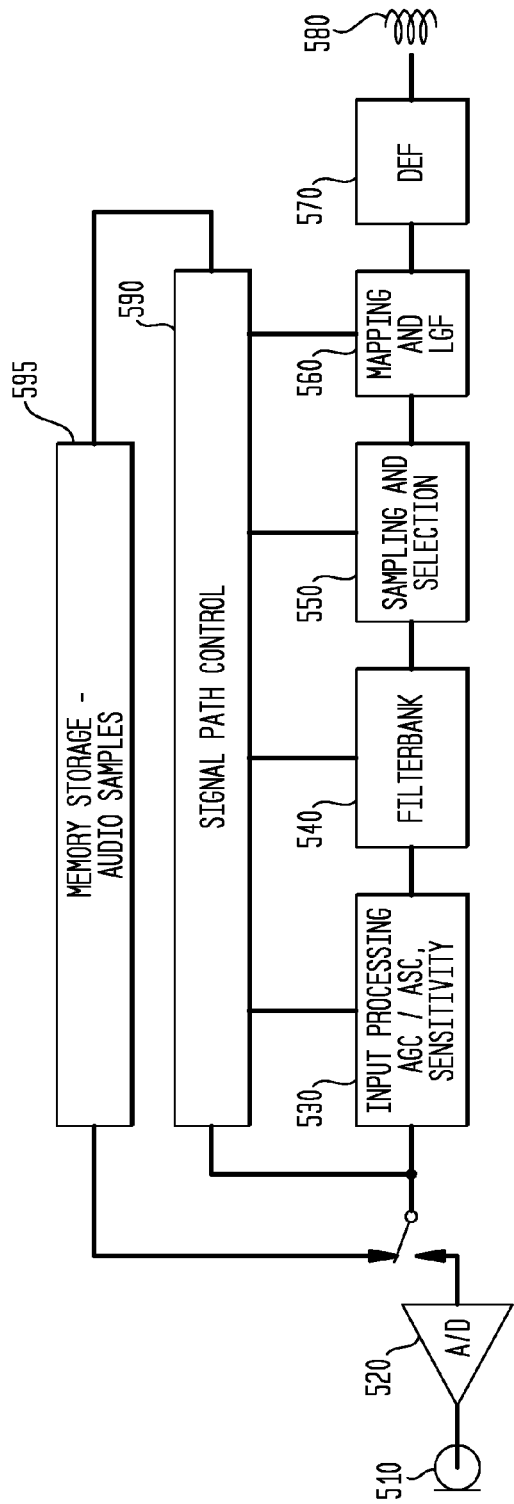

RECORDING AND RETRIEVAL OF SOUND DATA IN A HEARING PROSTHESIS

CROSS-REFERENCE TO RELATED APPLICATIONS

This application is a divisional application of U.S. patent application Ser. No. 13/461,182, entitled "Recording and Retrieval of Sound Data in a Hearing Prosthesis", filed on May 1, 2012, which is a divisional of U.S. patent application Ser. No. 11/402,836 entitled "Recording and Retrieval of Sound Data in a Hearing Prosthesis", filed on Apr. 13, 2006, now U.S. Pat. No. 8,170,677, which claims the priority of Australian Patent No. 2005901833 entitled, "Enhanced Hearing Prosthesis System," filed Apr. 13, 2005, and Australian Patent No. 2006900982 entitled, "Hearing Prosthesis with Improved System Interface" filed Feb. 28, 2006," which are hereby incorporated by reference herein in their entireties.

The present application makes reference to is related to International Publication Nos. WO0097/001314 and WO2002/054991, and U.S. Pat. Nos. 4,532,930, 6,537,200, 6,565,503, 6,575,894 and 6,697,674, which are hereby incorporated by reference herein in their entireties.

BACKGROUND

1. Field of the Invention

The present invention relates generally to hearing prostheses, and more particularly, to recording and retrieval of sound data in a hearing prosthesis.

2. Related Art

Hearing loss, which may be due to many different causes, is generally of two types, conductive and sensorineural. In some cases, a person may have hearing loss of both types. Conductive hearing loss occurs when the normal mechanical pathways to provide sound to hair cells in the cochlea are impeded, for example, by damage to the ossicles. Conductive hearing loss is often addressed with conventional auditory prostheses commonly referred to as hearing aids, which amplify sound so that acoustic information can reach the cochlea.

In many people who are profoundly deaf, however, the reason for their deafness is sensorineural hearing loss. This type of hearing loss is due to the absence or destruction of the hair cells in the cochlea which transduce acoustic signals into nerve impulses. Those suffering from sensorineural hearing loss are thus unable to derive suitable benefit from conventional hearing aids due to the damage to or absence of the mechanism that naturally generates nerve impulses from sound. As a result, hearing prostheses have been developed to provide persons with sensorineural hearing loss with the ability to perceive sound.

Hearing prostheses include but are not limited to hearing aids, auditory brain stimulators, and Cochlear™ prostheses (commonly referred to as Cochlear™ prosthetic devices, Cochlear™ implants, Cochlear™ devices, and the like; simply cochlea implants herein.) Cochlear implants use direct electrical stimulation of auditory nerve cells to bypass absent or defective hair cells that normally transduce acoustic vibrations into neural activity. Such devices generally use an electrode array inserted into the scala tympani of the cochlea so that the electrodes may differentially activate auditory neurons that normally encode differential pitches of sound. Auditory brain stimulators are used to treat a smaller number of recipients with bilateral degeneration of the auditory nerve. For such recipients, the auditory brain stimulator provides stimulation of the cochlear nucleus in the brainstem.

Cochlear implants typically comprise external and implanted or internal components that cooperate with each other to provide sound sensations to a recipient. The external component traditionally includes a microphone that detects sounds, such as speech and environmental sounds, a speech processor that selects and converts certain detected sounds, particularly speech, into a coded signal, a power source such as a battery and an external transmitter antenna.

The coded signal output by the speech processor is transmitted transcutaneously to an implanted receiver/stimulator unit, commonly located within a recess of the temporal bone of the recipient. This transcutaneous transmission occurs via the external transmitter antenna which is positioned to communicate with an implanted receiver antenna disposed within the receiver/stimulator unit. This communication transmits the coded sound signal while also providing power to the implanted receiver/stimulator unit. Conventionally, this link has been in the form of a radio frequency (RF) link, although other communication and power links have been proposed and implemented with varying degrees of success.

The implanted receiver/stimulator unit also includes a stimulator that processes the coded signal and outputs an electrical stimulation signal to an intra-cochlea electrode assembly. The electrode assembly typically has a plurality of electrodes that apply electrical stimulation to the auditory nerve to produce a hearing sensation corresponding to the original detected sound. Because the cochlea is tonotopically mapped, that is, partitioned into regions each responsive to stimulation signals in a particular frequency range, each electrode of the implantable electrode array delivers a stimulating signal to a particular region of the cochlea.

In the conversion of sound to electrical stimulation, frequencies are allocated to stimulation channels that provide stimulation current to electrodes that lie in positions in the cochlea at or immediately adjacent to the region of the cochlear that would naturally be stimulated in normal hearing. This enables the prosthetic hearing implant to bypass the hair cells in the cochlea to directly deliver electrical stimulation to auditory nerve fibers, thereby allowing the brain to perceive hearing sensations resembling natural hearing sensations.

While developments in signal processing continue to improve the capability of conventional cochlear implant systems to augment or provide an approximate sense of hearing for profoundly deaf persons, it has been found that conventional systems are inherently limited in their ability to fully restore normal hearing. It is desired to improve upon existing arrangements to enable recipients to better perceive and/or understand sounds of interest.

SUMMARY

In one aspect of the present invention, a hearing prosthesis for delivering stimuli to a hearing-impaired recipient is disclosed, the hearing prosthesis comprising: a sound transducer for converting received sound signals into electric audio signals; a sound processor for converting said electric audio signals into stimuli signals; a stimulator for delivering said stimuli to the recipient; a memory for storing data representative of sound signals; and a controller configured to cause selected sound data to be retrieved from said memory and processed by said sound processor.

In another aspect of the present invention, a sound processor for a hearing prosthesis having a sound transducer for converting received sound signals into electric audio signals and a stimulator for delivering stimuli to a recipient is disclosed, the sound processor comprising: a digital signal processor for converting said electric audio signals into stimuli signals; and a storage and retrieval system comprising a memory for storing sound data representative of sound signals, a data storage module for recording selected sound data, and a data retrieval module configure to retrieve selected data from said memory to be processed by said sound processor.

In a further aspect of the present invention, a method for delivering stimuli to a hearing-impaired recipient, comprising: converting received sound signals into electric audio signals; converting said electric audio signals into stimuli signals; delivering said stimuli signals to the recipient; storing data representative of said received sound signals; retrieving selected sound data from said memory; and processing said retrieved sound data by said sound processor.

BRIEF DESCRIPTION OF THE DRAWINGS

Embodiments of the present invention are described herein in conjunction with the accompanying drawings, in which:

FIG. 2A is a functional block diagram of a sound processor implemented in the sound processing unit illustrated in FIG. 1 in accordance with one embodiment of the present invention;

FIG. 2B is a functional block diagram of the sound data storage and retrieval system illustrated in FIG. 2A in accordance with one embodiment of the present invention;

FIG. 3B is a flow chart of the operations performed by the sound data storage and retrieval system illustrated in FIG. 2B in accordance with one embodiment of the present invention;

FIG. 3C is a flow chart of the operations performed by the internal component assembly illustrated in FIG. 1 in accordance with one embodiment of the present invention.

FIG. 4 is a block diagram illustrating a typical prior art cochlear implant;

FIG. 5 is a block diagram illustrating a one embodiment of another aspect of the present invention for a cochlear implant;

DETAILED DESCRIPTION

Figure 1:
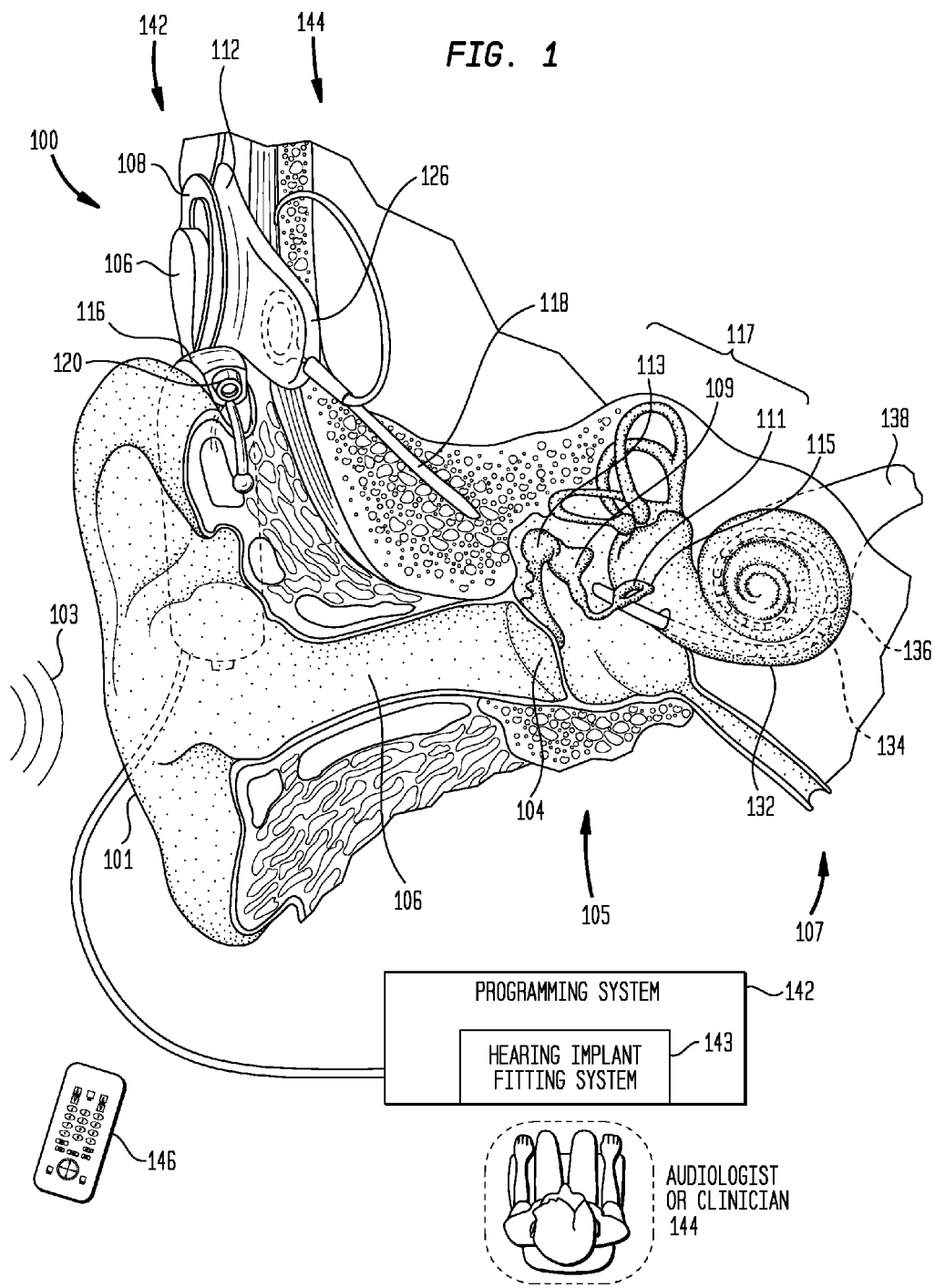
FIG. 1 is a schematic block diagram of an exemplary hearing prosthesis, a cochlear implant, in which embodiments of the present invention may be advantageously implemented.

FIG. 1 is a perspective view of an exemplary hearing prosthesis in which the present invention may be implemented. The relevant components of outer ear 101, middle ear 105 and inner ear 107 are described next below, followed by a description of an implanted cochlear implant 100. An acoustic pressure or sound wave 103 is collected by outer ear 101 (that is, the auricle) and channelled into and through ear canal 102. Disposed across the distal end of ear canal 102 is a tympanic membrane 104 which vibrates in response to acoustic wave 103.

This vibration is coupled to oval window or fenestra ovalis 115 through three bones of middle ear 105, collectively referred to as the ossicles 117 and comprising the malleus 113, the incus 109 and the stapes 111. Bones 113, 109 and 111 of middle ear 105 serve to filter and amplify acoustic wave 103, causing oval window 115 to articulate, or vibrate. Such vibration sets up waves of fluid motion within cochlea 132. Such fluid motion, in turn, activates tiny hair cells (not shown) that line the inside of cochlea 132. Activation of the hair cells causes appropriate nerve impulses to be transferred through the spiral ganglion cells (not shown) and auditory nerve 138 to the brain (not shown), where they are perceived as sound.

Cochlear prosthesis 100 comprises external component assembly 142 which is directly or indirectly attached to the body of the recipient, and an internal component assembly 144 which is temporarily or permanently implanted in the recipient.

External assembly 142 typically comprises a sound transducer 120 for detecting sound, and for generating an electrical audio signal, typically an analog audio signal. In this illustrative embodiment, sound transducer 120 is a microphone. In alternative embodiments, sound transducer 120 may comprise, for example, more than one microphone, one or more a telecoil induction pickup coils or other device now or later developed that may detect sound and generate electrical signals representative of such sound.

External assembly 142 also comprises a speech processing unit 116, a power source (not shown), and an external transmitter unit 106. External transmitter unit 106 comprises an external coil 108 and, preferably, a magnet (not shown) secured directly or indirectly to the external coil 108.

Speech processing unit 116 processes the output of microphone 120 that is positioned, in the depicted embodiment, by outer ear 101 of the recipient. Speech processing unit 116 generates coded signals, referred to herein as a stimulation data signals, which are provided to external transmitter unit 106 via a cable (not shown). Speech processing unit 116 is, in this illustration, constructed and arranged so that it can fit behind outer ear 101. Alternative versions may be worn on the body or it may be possible to provide a fully implantable system which incorporates the speech processor and/or microphone into the internal component assembly 144.

Internal components 144 comprise an internal receiver unit 112, a stimulator unit 126 and an electrode assembly 118. Internal receiver unit 112 comprises an internal transcutaneous transfer coil (not shown), and preferably, a magnet (also not shown) fixed relative to the internal coil. Internal receiver unit 112 and stimulator unit 126 are hermetically sealed within a biocompatible housing. The internal coil receives power and data from external coil 108, as noted above. A cable or lead of electrode assembly 118 extends from stimulator unit 126 to cochlea 132 and terminates in an array 134 of electrodes 136. Signals generated by stimulator unit 126 are applied by electrodes 136 to cochlea 132, thereby stimulating the auditory nerve 138.

In one embodiment, external coil 108 transmits electrical signals to the internal coil via a radio frequency (RF) link. The internal coil is typically a wire antenna coil comprised of at least one and preferably multiple turns of electrically insulated single-strand or multi-strand platinum or gold wire. The electrical insulation of the internal coil is provided by a flexible silicone molding (not shown). In use, internal receiver unit 112 may be positioned in a recess of the temporal bone adjacent to outer ear 101 of the recipient.

Further details of the above and other exemplary prosthetic hearing implant systems in which embodiments of the present invention may be implemented include, but are not limited to, those systems described in U.S. Pat. Nos. 4,532,930, 6,537,200, 6,565,503, 6,575,894 and 6,697,674, which are hereby incorporated by reference herein in their entireties. For example, while cochlear implant 100 is described as having external components, in alternative embodiments, cochlear implant 100 may be a totally implantable prosthesis. In one exemplary implementation, for example, sound processing unit 116, including microphone 120, a sound processor and/or a power supply may be implemented as one or more implantable components.

As shown in FIG. 1, cochlear implant 100 is further configured to interoperating with a wireless user interface 146 and an external processor 142 such as a personal computer, workstation or the like, implementing, for example, a hearing implant fitting system. This is described in greater detail below.

FIG. 2A is a functional block diagram of one embodiment of a sound processor 200 implemented in speech processing unit 116.

Sound processor 200 receives an electrical audio signal, typically an analog audio signal, from sound transducer 120 such as microphone.

Sound processor 200 comprises a signal conditioning and digital conversion module 202. The analog electrical audio signal 220 is processed by conditioner and analog-to-digital (A/D) converter 202. Initially, conditioner and A/D converter 202 conditions analog electrical audio signal 220 and converts it into a digital audio signal 222.

Sound processor 200 further comprises a digital signal processor (DSP) 204 configured to perform complex digital signal processing operations on digital audio signal 222. DSP 204 generates a processed digital audio signal 224. It will be appreciated by those of ordinary skill in the art that DSP 204 may implement digital signal processing techniques now or later developed to generate processed audio signal 224.

Following the above-noted digital signal processing operations, a sound data-to stimulus data converter 206 converts processed audio signal into a stimulation signal suitable for delivery to stimuli transducers, such as electrodes 136 (FIG. 1). Typically, during this conversion stage, recipient-specific parameters are applied to the signal to customize the electrical stimulation signals for the particular recipient's requirements.

Today, most cochlear implants require values for at least two recipient-specific parameters to be set for each stimulating electrode 136. These values are referred to as the Threshold level (commonly referred to as the "THR" or "T-level;" "threshold level" herein) and the Maximum Comfortable Loudness level (commonly referred to as the Most Comfortable Loudness level, "MCL," "M-level," or "C;" simply "comfort level" herein). Threshold levels are comparable to acoustic threshold levels while comfort levels indicate the level at which a sound is loud but comfortable. It should be appreciated that although the terminology and abbreviations may not be used in connection with all cochlear implants, the general purpose of threshold and comfort levels is common among cochlear implants: to determine a recipient's electrical dynamic range.

These and other customizing parameters are normally determined in consultation with a clinician, audiologist or other practitioner 144 ("clinician" herein) during a clinical "mapping" procedure using a hearing implant fitting system 142. Sound data-to-stimulus data converter 206 may implement stimulation signal conversion and parameter customization operations as presently employed in commercial hearing prostheses as well as such techniques as developed in the future. As one of ordinary skill in the art would appreciate, such operations performed by conventional hearing prosthesis systems are well-known and, therefore, are not described further herein.

Stimulus signal 226 generated by sound data-to-stimulus data converter 206 is applied to a stimulus data encoder 208 and link signal generator 210. Stimulus data encoder 208 encodes the stimulation signal, and the encoded signals are provided to link signal transmitter 210 for transmission to implanted stimulator unit 126. In the embodiment described above with reference to FIG. 1, such transmission occurs over a transcutaneous link. In such embodiments, link signal transmitter 210 comprises external coil 108 (FIG. 1) and related components.

The above-noted sound processing operations and stages 202, 204, 206 and 208 are subject to control from a system controller 212. As one of ordinary skill in the art will appreciate, sound processor 200 may be used in combination with any speech strategy now or later developed, including but not limited to, Continuous Interleaved Sampling (CIS), Spectral PEAK Extraction (SPEAK), and Advanced Combination Encoders (ACE™). An example of such speech strategies is described in U.S. Pat. No. 5,271,397, the entire contents and disclosures of which is hereby incorporated by reference herein. The present invention may also be used with other speech coding strategies now or later developed. In one embodiment, the present invention may be used on Cochlear Limited's Nucleus™ implant system that uses a range of coding strategies alternatives, including SPEAK, ACE™, and CIS. Among other things, these strategies offer a trade-off between temporal and spectral resolution of the coded audio signal by changing the number of frequency channels chosen in the signal path.

System controller 212, in concert with other components of cochlear implant 100, ensures that the time delay between sound signals 103 being received by sound transducer 120 and the delivery of corresponding stimuli at implanted electrodes 136 is maintained within acceptable limits. Too much time delay can cause discomfort and disorientation for the recipient. In particular, when this delay is excessive the recipient can experience further difficulties in interpreting or understanding speech and other sounds of interest, particularly in the presence of extraneous noise or echoes.

Hence, the minimization of such time delay improves the real-time performance of cochlear prosthesis 100. This may significantly limit the extent to which incoming sound 103 can be processed, particularly given the limited battery power available in small, light weight prostheses.

System controller 212 also comprises a sound storage and retrieval system 228 constructed and arranged to store sound data that is incorporated into the above-described sound processing pipeline to provide the recipient with information that supplements, compliments or facilitates the interpretation and understanding of sound 103. FIG. 2B is a functional block diagram of one embodiment of sound data storage and retrieval system 228 illustrated in FIG. 2A. Embodiments of system 228 will now be described with reference to FIGS. 2A and 2B.

Sound storage and retrieval system 228 configured to store or record sound data 230A-230D selected from a sound processing stage 202, 204, 206, 208, respectively. Recorded sound data 230 may be stored with associated data (described below) in accordance with configurable storage settings. System 228 also retrieves selected sound data 232A-232D for delivery to an appropriate sound processing stage 202, 204, 206, 208, respectively. Retrieved sound data 232 may be processed as necessary by sound processor 200 to generate desired stimuli to the recipient reflecting the retrieved sound signals 232.

In the embodiment illustrated in FIGS. 2A and 2B, sound data storage and retrieval system 228 exchanges data and commands with system controller 212 of sound processor 200, as shown by data/command line 234. Sound data storage and retrieval system 228 also exchanges data and commands with programming system 142 (FIG. 1) via a programming interface 214, as shown by data/command line 236, and user interface(s) 216 controllable by the recipient.

As will be appreciated by those of ordinary skill in the art, user interface 216 can take many different forms. For example, user interface 216 can include a keypad allowing the recipient to enter necessary commands. Alternatively, user interface 216 may allow different forms of interaction with the recipient to invoke commands, such as voice command recognition, head tilt or other user gesture recognition, etc. User interface 216 may be physically connected to the system. Alternatively or additionally, user interface 216 can be in the form of a wired or wireless remote control unit 146 (FIG. 1).

As shown in FIG. 2B, sound data storage and retrieval system 228 comprises one or more memory modules 258 for storing sound data in accordance with the teachings of the present invention.

As one of ordinary skill in the art would appreciate, memory module(s) 258 may comprise any device, component, etc., suitable for storing sound data 230 as described herein. For example, memory module(s) 214 may comprise computer-readable media such as volatile or non-volatile memory. Also, memory module(s) 258 may comprise removable memory module(s) 258A, permanent or non-removable memory modules 258B, as well as remove memory module(s) 258C not collocated with system 228 or, perhaps, sound processor 200.

As will be described in greater detail below, one advantage for using removable memory module(s) 258A such as a flash memory module is that the recipient or the recipient's clinician or audiologist can be provided access to the sound data stored therein for processing or analysis.

Sound data storage and retrieval system 228 determines which memory module(s) 258 to store sound data based on a memory module selection command 264. Memory module selection command 264 may be generated by any of the components or devices which system shares an interface such as system controller 212, sound processor user interfaces 216, etc. As one of ordinary skill in the art would appreciate, sound data storage module 252 may automatically select which memory module 258 based on other commands, data or circumstances. For example, if the user selects a certain data format or compression scheme, the resulting recorded sound data 230 may be stored on one type of memory module 258. In another example, should one type of memory module 258 not have sufficient memory available to store sound data, then sound data storage module 258 selects an alternative memory module 258 in which to store recorded sound data 230.

Referring to FIG. 2A, recorded sound data 230 may comprises one or more of analog audio signal 220 generated by sound transducer 120, digital audio signal 222 generated by condition and ADC module 202, processed audio signal 224 generated by DSP 204, and stimulation signal 226 generated by converter module 206. In other words, sound data storage module 252 may record data from any stage along the sound processing pipeline, including sound data which has not been processed (that is, analog audio signal 220 and digital audio signal 222) and sound data which has been processed (that is, processed audio signal 224 and stimulation signal 226).

As noted, sound data-to-stimulus data converter 206 converts processed audio signal 224 into a stimulation signal 226 suitable for delivery to electrode array 134, and that such operations typically include the application of user-specific parameters to customize the electrical stimulation signals for the particular recipient. As a result, in embodiments described herein in which sound data 230 stored in memory module(s) 214 includes sound data 230D having a content as that of stimulation signal 226, recipient-specific parameters are either not utilized or recipient-specific parameters are applied to stimulation signal 226 prior to its storage in memory module(s) 214.

It should also be appreciated that sound data storage module 252 records sound data that is representative of 'live' sounds; that is, sound signals currently being received by sound transducer 120 and which is not processed, partially processed or completely processed by sound processor 200. In other words, embodiments of sound data storage and retrieval system 228 are capable of effectively making live sound recordings.

As shown in FIG. 2B, sound data storage module 252 receives for storage sound data 260 from programming system 142 via programming interface 214 and sound data 262 from removable memory module 258A. As such, removable storage media may also be used to store recorded entertainment such as MP3 music files, allowing the recipient to enjoy such program material thus avoiding the inconvenience of additional devices and interconnecting cables.

In addition to the source of sound data 230, sound data storage and retrieval system 252 may also be configured to record the selected sound data in accordance with a specified recording period 270. Recording period selection command 270 specifies the particular portion of the identified source data 230A-230D which is to be recorded. For example, the selected sound data may be recorded between a begin record and end record indication, at certain specified time periods, continuously, for a specified duration, and the like.

Sound data storage and retrieval system 228 determines the content and duration of recorded sound data 230 based on a sound data content selection command 268 and a recording period selection command 270. Commands 268 and 270 may be generated by any of the components or devices which system shares an interface such as system controller 212, sound processor user interfaces 216, etc. As one of ordinary skill in the art would appreciate, sound data storage module 252 may automatically select which stage 120, 202, 204, 206, 208 or 210 from which sound data 230 is to be recorded based on other commands, data or circumstances.

Sound data storage module 252 is further configured to store recorded sound data 230 in any format (including compression) desired or required. For example, sound data can be stored in any one of several different formats depending on the sound data content, storage settings 272. Storage settings 272 may be provided by the recipient, via user interfaces 214 or via programming device 142. In one embodiment, the choice of data storage format is made continuously and automatically by sound processor 200 or other component of hearing prostheses 100, and provided to sound data storage and retrieval system 228 via, for example, system controller 212. In such an embodiment, the assigned data storage format might therefore change in real-time to accommodate changing conditions.

Such data formats may include, but are not limited to a continuous or intermittent serial bit stream representing the original sound signal, compressed MP3 format, indexed regular expression types of data compression, sound feature extraction and compression in time and frequency domain, or data representing the stimulation current which might be delivered to the recipient.

The format and compression may be selected, for example, so as to optimize various operating parameters which include data storage capacity, storage rate, retrieval speed and battery energy consumption efficiency. For example, in one embodiment the format of recorded sound data 230 is selected so as to allow one or more days of sound to be continually recorded using low sample rates and MP3-type sound data compression.

In addition to storing recorded sound data 230, sound data storage module 252 also stores associated data 274 prior to, simultaneously with, or subsequent to the storage of recorded sound data 230.

In some embodiments, associated data 274 comprises one or more labels, so that the recipient can select which recorded sounds 230 are to be retrieved and processed by sound processor 200. In one embodiment, for example, associated data 274 comprises a timestamp that may be used to trigger the retrieval of sounds recorded at a selected time.

In another embodiment, associated data 274 includes a difficult status or rating provided by the recipient. Such information can be utilized, for example, when the sound data storage and retrieval system 228 is continuously recording sound data 230. During such real-time recording, the recipient can identify which recorded sound data 230 includes sounds the recipient had difficulty perceiving. Hence, the recipient, upon encountering a problem in perceiving a 'live' sound, may, for example, press a button on a user interface 214 which causes system 228 to label the current or last stored recording with an indication that a difficult sound is included. Such relabelling will assist in retrieving the recording for later retrieval and play back. Potentially, also, such relabelling could assist in a clinical analysis by a hearing specialist 144.

In effect, this allows the recipient to 'replay' sounds previously provided as stimuli. In this way, if a recipient missed sounds the first time, the recipient can command the system to replay the recorded sound data, repetitively if desired. In the embodiment illustrated in FIG. 2B, such a selection is provided to sound data retrieval module 254 as a selection criteria command 280 provided, for example, via user interfaces 216 or programming interface 214.

In the same or other embodiments, recorded sound data 230 is labelled with a file name, a time stamp to indicate the date and time of day when the data was acquired and stored, and a summary of the data content of the file. Such summary can include, but is not limited to, the duration of a sound data recording, spoken words or phrases which might be attached by a recipient to facilitate latter retrieval, or key sounds or phrases identified by the recipient at the time they were heard and recorded.

The recipient may also provide sound data retrieval module 254 with a replay characteristics command 282. For example, replayed sounds can be presented to the recipient at a different apparent replay speed and pitch from the original sound 103 as specified in command 282. Slowing the rate at which a recorded conversation is presented to the recipient while raising the pitch of low frequency voice formants can greatly increase the recipient's comprehension of speech. Similarly, the duration of any pauses in recorded speech may be increased or decreased at the recipient's discretion. As one of ordinary skill in the art would appreciate other characteristics of the retrieved sound 232 may be controlled in alternative embodiments of the present invention.

Once the desired recorded sound 230 is selected based on search criteria 280, and the desired playback characteristics are set based on replay characteristics 282, the recipient may initiate retrieved sound data 286 by generating replay command 284.

As shown in FIG. 2B, retrieved sound data 286 is provided to a data extractor module 254 to reconstitute the retrieved sound data into a form suitable for delivery to the desired destination 290 such as programming interface 214 or a particular stage 202, 204, 206, 208, 210 of the sound processor pipeline.

As noted, recorded sound data 230 may comprises one or more of analog audio signal 220 generated by sound transducer 120, digital audio signal 222 generated by condition and ADC module 202, processed audio signal 224 generated by DSP 204, and stimulation signal 226 generated by converter module 206. In other words, sound data storage module 252 may record data from any stage along the sound processing pipeline, including sound data which has not been processed (that is, analog audio signal 220 and digital audio signal 222) and sound data which has been processed (that is, processed audio signal 224 and stimulation signal 226).

As such, retrieved sound data 232 may or may not be processed by DSP 204. For example, if recorded sound data 230 is stored in a form representative of stimulation signals 226, the corresponding retrieved sound data 232 requires little or no processing and the retrieved stimulation signals may be provided directly to the implanted neural stimulator 126. Similarly, should recorded sound data 230 be stored in a form representative of digital audio signals 222, the corresponding retrieved sound data 232 will be processed by the remaining portions of the sound processor pipeline, namely DSP 204, converter 206, encoder 208 to form electrical stimulation signals as described above.

It should be appreciated that in certain embodiments or under certain circumstances while stored sounds are being retrieved and processed by sound processor 200, real-time or "live" sounds received via sound transducer 120 are not simultaneously processed through sound processor 200 and provided as stimuli to the recipient. As such, when sound data storage and retrieval system 228 is invoked to retrieve sound data 232, system controller 212 temporarily interrupts or reduces the perceivable level of live sound 103 in some embodiments of the present invention.

This ability to selectively recall sounds of interest is particularly beneficial for recipients of hearing prostheses that use electrical stimulation either whole or in part, to evoke a hearing or hearing-like sensation. The successful habilitation of such recipients can be limited by the spatially discontinuous manner in which a finite number of stimulating electrodes 136 of the implanted neural stimulator 126 can stimulate the recipient and invoke a realistic sense of hearing. This may improve outcomes for such recipients by providing a different approach to improving the habilitation and/or ability to recognize noises.

Sounds that have been stored and identified by the recipient as difficult to understand can, for example, be recalled and uploaded to a computer then emailed to the user's hearing professional 144. Subsequent analysis would then empower the hearing professional to refine prosthesis settings to better serve the recipient's future understanding of such identified sounds.

As an illustrative example of a scenario where this is of benefit, picture a recipient in a noisy environment, for example a train station, and a message is announced on the public address system. Due to the limitations imposed on sound processor 200 for approximate real-time processing of live sounds, the important sounds, that is, the announcement, may not be perceived clearly by the recipient. By 'replaying' the stored data representative of when the announcement happened and allowing the processor more time to conduct more complex processing, the announcement can be perceived more clearly with much of the background noise eliminated.

As another illustrative example; a recipient encounters an environmental sound such as the ring of a doorbell. The recipient may be unable to interpret this sound if sound processor 200 is configured to optimize human speech while excluding background noise. By activating the re-call control, the sound of the doorbell can be played back to the recipient, only this time using speech processor settings intended to optimize environmental sounds.

A further benefit of the 'record' and 'replay' functionality arises in speech habilitation. Impaired speech frequently arises in persons with compromised hearing, as they are unable to accurately hear and compare their own voice to that of others. With the present system, a recipient can 'record' their own voice and selectively 'replay' the recording to hear what their voice sounds like. In this way, recipients can capture, identify and correct the parts of their own speech which others find difficult to understand.

In another embodiment, a sound recognition comparator 215 detects when an incoming or replayed sound, or the attributes of an incoming or replayed sound, closely match those of a sound, or collection of sound attributes, stored previously. In the embodiment shown in FIG. 2A, sound recognition comparator 215 is included in system controller 212, although that need not be the case.

The recognition of specific sounds or categories of specific sounds can be used to trigger functional changes in the operation of the prosthesis, for example adjustment of control settings of sound processor 200 in response to commands spoken by the recipient or others.

Additionally or alternatively, the recognition of specific sounds or categories of specific sounds can be used to deliver a different or substitute sound in response to that of a recognized sound. Spoken phrases substituted for incoming sound can alert the recipient about the approach of a speeding motor vehicle, the sound of a door bell or the cry of a baby. In this way, translation from one spoken language to another can be implemented.

Aside from recipient-initiated 'play' of stored sounds, there can be benefits from having automatically triggered 'play' of stored sounds. As an example, certain types of sounds may be of particular interest to the recipient, e.g. a telephone ringing, a baby crying or a fire alarm. In which case, it is important to the recipient that such sounds are perceived, or when not perceived their occurrence is alerted to the recipient. In exemplary embodiments of the present invention, the sound recognition comparator 215 recognizes such important sounds from the incoming electric audio signal. In the event of an important sound being detected, sound data storage and retrieval system 228 can be triggered to retrieve respective data from memory module(s) 258. The respective data stored may be an isolated recording of the important sound. Alternatively, the data stored could be a voice recording made by the recipient describing the important sound, e.g. "my baby is crying", "the fire alarm is sounding", "the telephone is ringing". In such embodiments, user interface 216 may include some form of programming function to allow a recipient to program the system to recognize particular sounds and label particular stored data to be triggered in response to such sounds being detected.

When the data is stored in the format of electric audio signals 252 or 254, sounds which are to be 'replayed' are reprocessed by sound processor 200. Since the 'replayed' sounds are not required to be processed in approximate real time, more time may be given to the reprocessing which allows more complex or different processing to be applied. In this manner, the 'replayed' sounds are provided as stimuli to the recipient with improved clarity than when the sounds were originally processed in real-time. Such additional processing is attained by system controller 212 controlling the pertinent stages 202, 204, 206, 208, 210 of the sound processing pipeline. In one embodiment, repetitive processing is attained by data extractor 256 converting retrieved sound data 232 to the content necessary for processing by the desired stages, including DSP stage 204, of the sound processing pipeline.

In some embodiments, the playing of sounds can include the reconstruction of voice sound signals from data stored as ASCII text. In certain embodiments, sound data extractor module 256 also comprises a speech synthesizer such as that described in International Publication Nos. WO0097/001314, which is hereby incorporated by reference herein, to convert such data to sound signals which may then be converted further, if necessary, for processing by the desired stages of the sound processing pipeline.

Figure 3A:
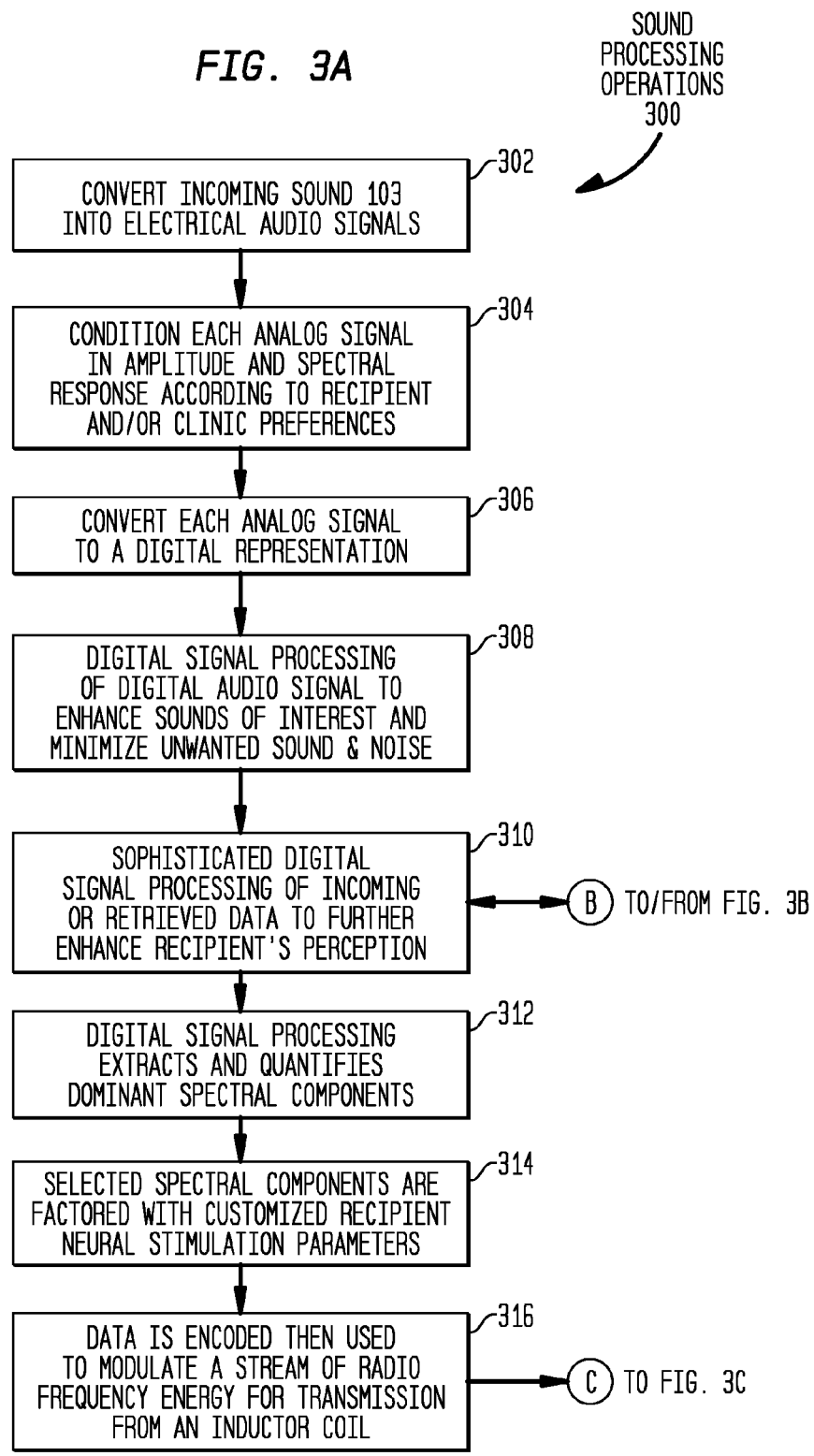
FIG. 3A is a flow chart of the operations performed by the sound processor illustrated in FIG. 2A in accordance with one embodiment of the present invention.

FIG. 3A is a flow chart of certain aspects of a process 300 in which operations of one embodiment of the present invention are performed.

At block 302, sound transducer 120 converts incoming sound into an analog electrical audio signal 220.

At block 304, analog signal 220 is conditioned in amplitude and spectral response, and then the conditioned analog signal is converted into a digital signal for further processing. The analog signal conditioning is conducted in accordance with customized parameters derived from a system control memory 402. Such customized parameters are optimized recipient-specific parameters which are typically established and programmed into system control memory 402 in consultation with a hearing clinician. The resulting audio signal is digitized at block 306.

At block 308, the converted digital signal 222 is processed by DSP 204 to enhance sounds of interest and to minimize unwanted sounds and noise. The customized parameter control is derived from system control memory 350.

At block 310, potentially more sophisticated digital signal processing is conducted on digital audio data 222 to further enhance the signal for the purposes of recipient perception. As noted, for "real time" signals there are limitations on the potential for conducting more sophisticated processing. Hence, at this stage in the process, it is convenient to provide the interaction with sound data storage and retrieval system 200, the operations of which are illustrated in FIG. 3B.

Preferably, all 'real time' data is continuously packaged 352, that is, labelled and formatted for storage, and then stored 354 into memory 258. Ideally, continuously stored data is stored in blocks of discrete time, for example, 60 seconds, of incoming sound 103.

At block 310, data retrieved from memory 258 may be subjected to the sophisticated digital processing. Data retrieval may be initiated by recipient selection, in which case the selected sound data is searched for and retrieved from memory. In exemplary embodiments, the data retrieval may be initiated automatically, for example where the 'real time' sound signal includes a predetermined sound signal which, upon detection, triggers the retrieval of corresponding stored data to be 'played' to the recipient in place of the live sound. In such cases, the processing at block 310 includes signal analysis to detect the presence of predetermined sounds, which may be derived from the system control memory 350 for the purpose of comparison.

Ideally, at block 310, where retrieved data is to be processed and provided to the recipient as perceivable stimuli, 'real time' signals are suppressed to prevent the recipient experiencing confusing output. However, while the 'real time' signals are suppressed, they are still packaged and stored for subsequent retrieval, if desired or required.

At block 312, the 'real time' digital signal or retrieved digital signal is further processed to extract and quantify dominant spectral components. Following this, at 314, selected spectral components are factored with customized recipient neural stimulation parameters, derived from system control memory 350, producing a stimulation signal.

In cases where sound processor 200 is separate from the implanted stimulator 126, the processed digital data is encoded at block 316 and converted for the purposes of wireless transmission 358 to implant stimulator 126 and its internal processes.

FIG. 3C is a flow chart of one embodiment of the operations performed in implanted assembly 144 of cochlear implant 100. At 380, the wireless transmission is received and converted into a digital signal representative of the stimulation signal. At 382, the digital signal is converted into discrete channels of stimulation signals which is then provided to the implant's electrode system to provide, at block 384, stimulating currents to the targeted neural stimulation sites of the recipient thereby providing perceivable sound to the user.

While the present invention has been described with reference to specific embodiments, it will be appreciated that various modifications and changes could be made without departing from the scope of the invention. For example, it is anticipated that the main functional elements of the present invention could be applied as an upgrade module for existing prosthesis systems. In this regard, it is expected that the processing, controller and memory components could be provided in the form of an upgrade module for replacing the processing and control capabilities of existing prosthesis systems. As another example, it should be appreciated that the allocation of the above operations are exemplary only and that the functions and operations of the present invention may be implemented in other or one single component, subsystem, or system. As just one example, sound data storage and retrieval system 228 may be implemented completely in system controller 212 in alternative embodiments of the present invention. As another example, sound data storage and retrieval system 228 other than memory modules 258 may be implemented in system controller 212 in alternative embodiments of the present invention. As another example, in alternative embodiments, sound processor 200 is incorporated into an auditory brain stem hearing prosthesis, or other neural stimulation implant device. In such embodiments, sound processor 200 is hard-wired with the prosthesis and the stimulation signals are provided directly to the device for application as stimuli to the neural hearing system of the recipient. Alternatively, the sound processor is physically separate from the implant device. In this case, the stimulation signals are provided by way of wireless signals from a transmitter, associated with the processor, to a receiver incorporated with the implant device. As a further example, in embodiments in which sound processor 200 is implemented in a hybrid hearing prosthesis that delivers electrical and mechanical (acoustical or electro-mechanical) stimulation to a recipient, retrieved sound data 232 may be recorded by one subsystem, for example, the cochlear prosthesis, and played back in another subsystem for possible improved perception. In a further example, in alternative embodiments, sound data storage and retrieval system 200 may be implemented by a file handling system. In another example, the above aspects of the present application are supplemented with features of International Publication No. WO97/01314 filed on Jun. 28, 1996 which is hereby incorporated by reference herein in its entirety. Accordingly, it will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Another aspect of the present invention is described next below with reference to FIGS. 4 through 17. In a broad form, this aspect of the present invention provides a speech-based interface between a sound processor and the recipient. The system generates speech, from recorded or other sources, which is supplied using the prosthesis to the recipient. Thus, the recipient will hear a message in understandable speech, for example 'battery low', rather than a series of tones.

This aspect of the present invention is principally described with reference to implementations for cochlear implants of conventional type. However, it will be understood that the present invention is broadly applicable to other types of hearing prostheses, such as brain stem implants, hearing aids and the like.

Generally, a sound processor would be able to 'speak' to the recipient to provide them with information as required by the system design. Information or warnings from the sound processor are issued to the recipient using recorded or generated speech segments. For example, the sound processor plays back a recorded speech sample, such as 'program 2' or 'battery low' when required.

This could also extend to a range of built in self check systems, diagnostics, implant test, remote control test, complicated feature or menu systems ("choose from the following options . . . "), etc. Once the facility is provided, it will be apparent that it can be used in a variety of circumstances.

Prior art FIG. 4 shows the basic signal processing path for a typical cochlear implant speech processor. Sound originates at microphone 410, is the digitized by one or more analog-to-digital converters (ADC) 420, possibly through an Automatic Gain Control (AGC) and sensitivity adjustment 430, through to a filter bank 440. The signal is then processed with a cochlear implant speech coding strategy, such as ACE, in the sampling and selection stage 450. The signals are then mapped 460 into the electrode map for the recipient, encoded by the data encoder formatter (DEF) 470, for transmission via the RF coil 480 to the implant. This is described so as to explain the basic, existing system without the addition of the present invention, so that the various implementations described below will be better understood. The operation of such an implant system as shown in FIG. 4 is well understood in the art, and is implemented in commercially available systems.

One implementation of this aspect of the present invention is shown in FIG. 5. Take for example a simple alarm condition with the speech processor, such as battery low. When the speech processor software or hardware detects this condition, signal path controller 590 becomes operative. It is noted that existing processors are arranged to determine and indicate this condition, and that the present embodiment is concerned with how this is communicated to the recipient.

According to the embodiment of FIG. 5, once the alarm condition is established, the microphone 510 is switched out of the input, so that a stored digital audio signal in memory 595 can be delivered to the speech processing system. The signal path controller 590 may also disable any adaptive functions in the signal path, such as compression, that would affect the playback of the sound. The signal path controller 590 would then select the required audio signal, and start the output of the memory into the signal path, replacing the usual input from the analog to digital converter 520.

It is also possible to mix the playback of the sound message with the incoming microphone audio. In either case, the recipient would hear the speech segment 'battery low' at a predefined volume level, which will provide a much more readily understood message than a set of beeps.

Figure 9:
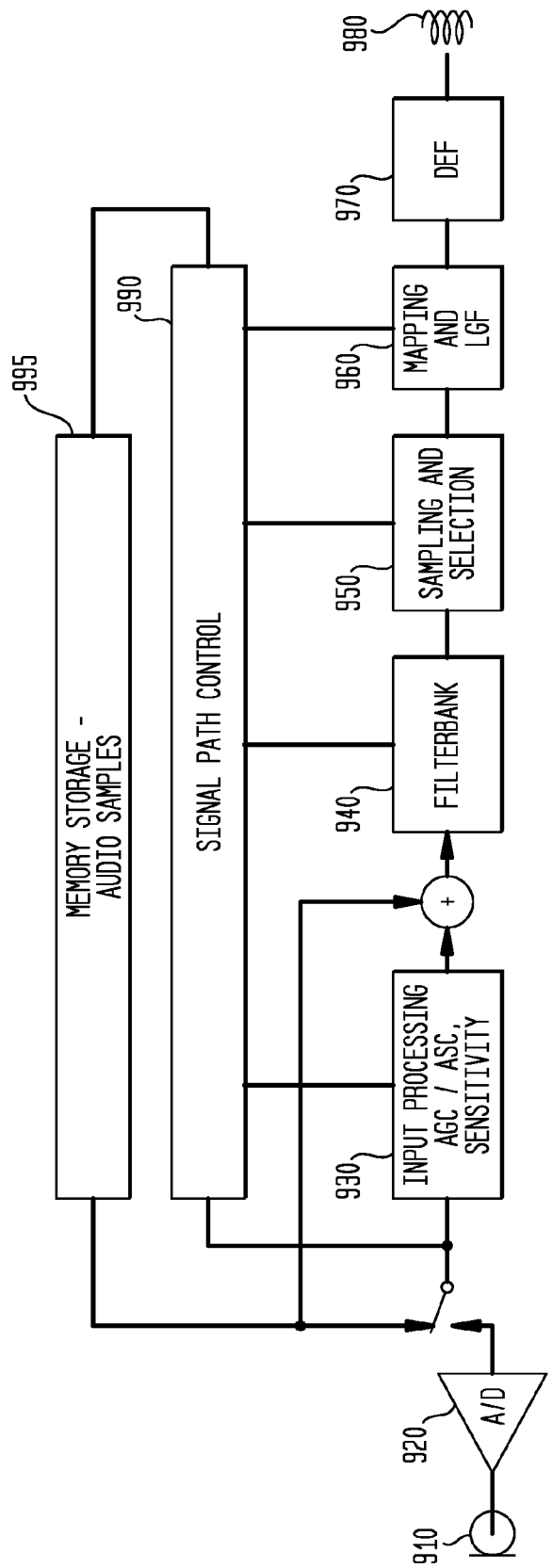
FIG. 9 is a block diagram illustrating another embodiment of this aspect of the present invention for a cochlear implant.

The ability to mix the playback of the sound message with the incoming microphone audio would provide minimal interruption to the environment being listened to by the recipient, since the signal from the microphone 510 is still heard. The amplitude ratio for which the two signals are combined could be programmable. A typical mixing ratio might be 3:1; that is, the microphone signal is set to a third of the amplitude of the sound message signal. The signal path controller 590 may also choose to mix the sound message in with the microphone signal at a point after the front end processing is complete, so that the sound message is not modified by these functions. This is shown in FIG. 9.

In order to ensure each sound message is always heard at a predefined volume level, a method could be applied whereby for example the RMS level of each sound message is adjusted before downloading to the speech processor to a set target level. During playback this target level is then mapped to a particular volume that is comfortable for the recipient. This level could be adjusted for each recipient as required.

One example of a complete operation of the sound message function being used for a 'battery low' alarm is given below in pseudo code:

```
If (Notification = True)          % There is an alarm condition
    % Setup the signal path for the sound message:
    Call SignalPathController(AGC=Off, ASC=Off); Call
    SignalPathController(MicrophoneSignal=Off);
    Alarm = IdentifyAlarm( );     % Find out which alarm
    Select Case (Alarm)           % Decide which message
    Case BattEmpty:
        CallPlayMessage(BATT_EMPTY_MESSAGE):
    Case BattLow:
        CallPlayMessage(BATT_LOW_MESSAGE);
    End Case;
    % Return the signal path to how it was before
    Call SignalPathController(AGC=On, ASC=On);
    Call SignalPathController(MicrophoneSignal = On);
Return;
```

The BATT_EMPTY_MESSAGE and BATT_LOW_MESSAGE values could be, for example, pointers to the required sampled speech data to be played.

Figure 6:
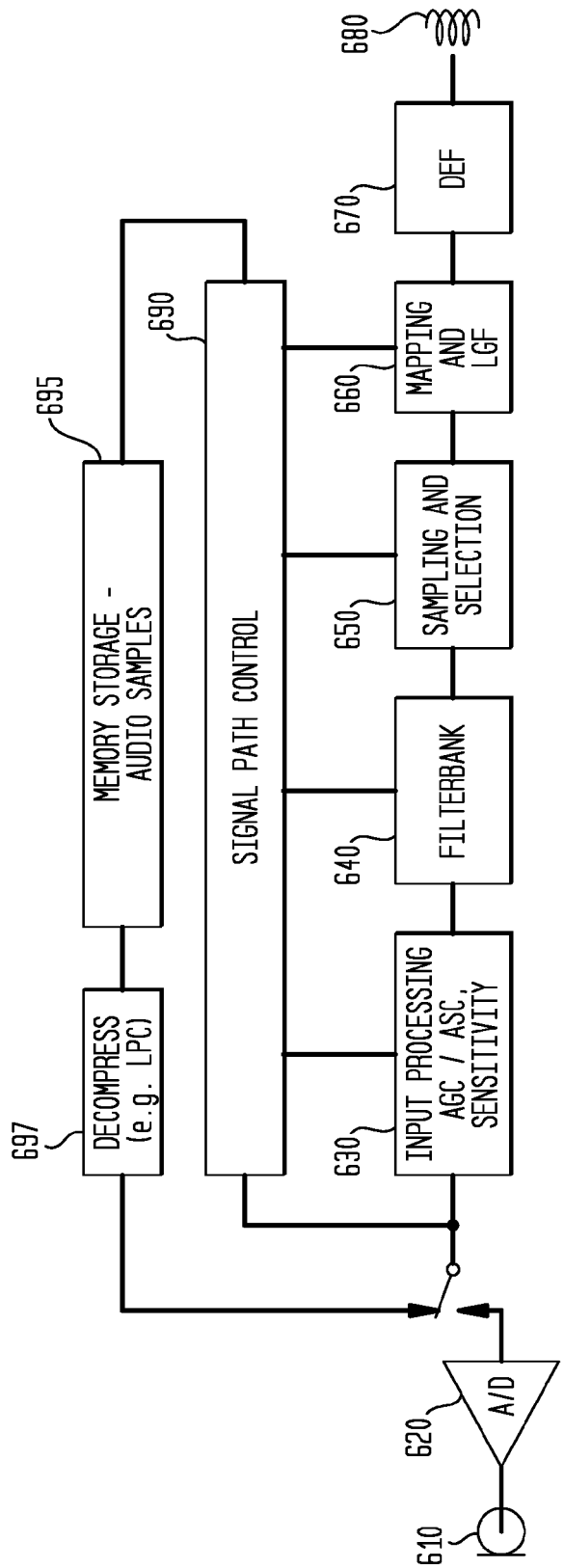
FIG. 6 is a block diagram illustrating another embodiment of this aspect of the present invention for a cochlear implant.
Figure 7:
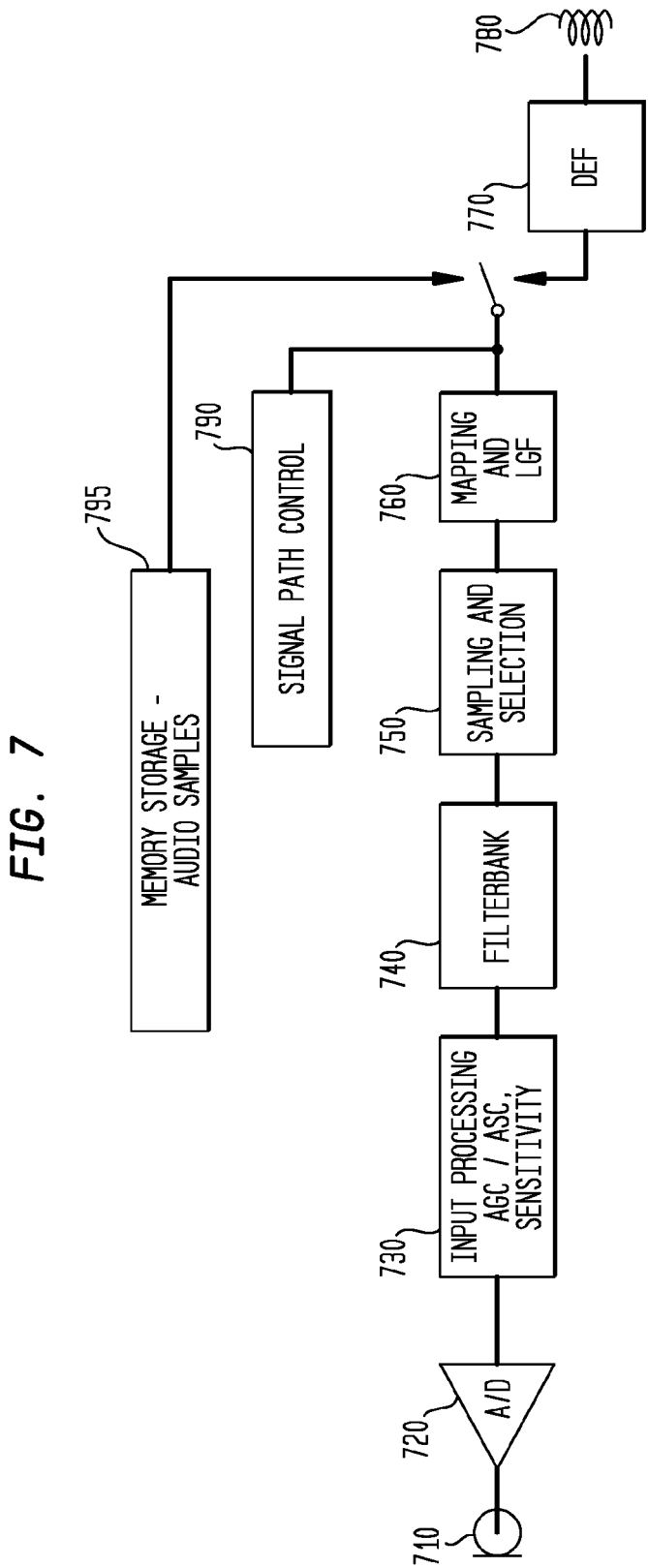
FIG. 7 is a block diagram illustrating another embodiment of this aspect of the present invention for a cochlear implant.

The data storage format of the sampled speech messages at its simplest implementation would be such that when played through the signal path, the sound is presented to the recipient as though received through the microphone 510. For example, if the ADC 520 in the system is a 16 bit 16000 Hz device, then the speech segments comprising each message should also be pre-recorded in this format, preferably with a similar type of microphone. However, this form of data may lead to storage issues with large digital files. One way to avoid this is to use speech compression to reduce the memory requirements needed, such as Linear Predictive Coding (LPC). Any type of conventional speech compression could be used. This would lead to a reduced memory requirement. FIG. 6 shows an implementation of this type, where an additional decompression stage 697 is required.

Figure 10:
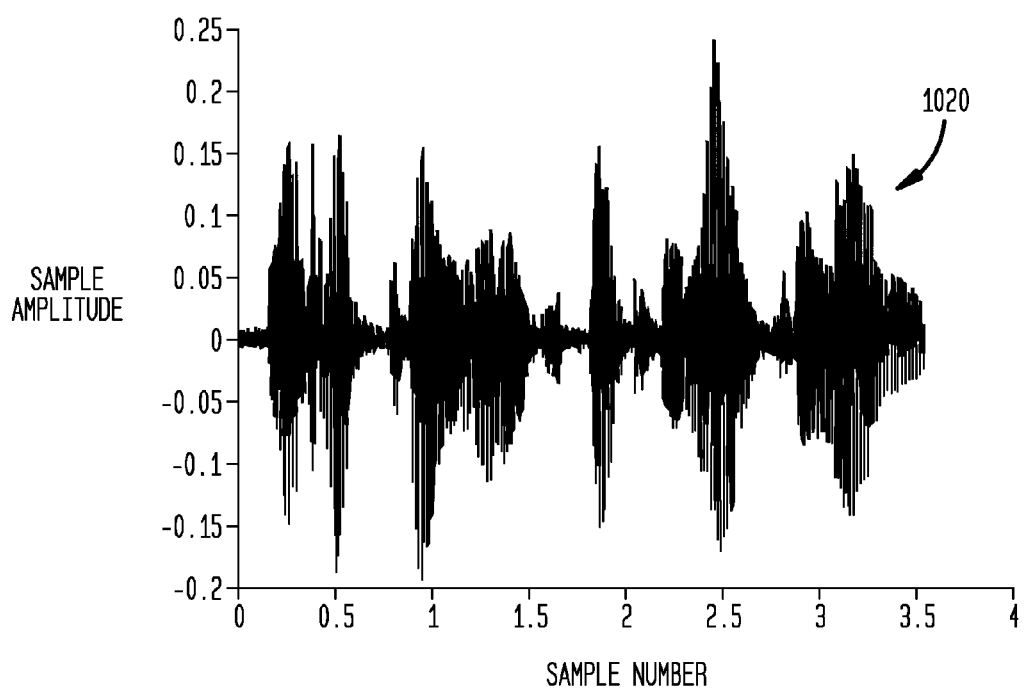
FIG. 10 is an exemplary waveform for a segment of speech.

By way of example, a message that might be required to be implemented in the system is the segment of speech "You have 10 minutes battery life remaining". An example waveform 1020 of this segment is shown in FIG. 10, which was recorded with a standard PC sound card at 16000 Hz sampling rate, 16 bit resolution, and with one channel of audio (mono). The segment lasts approximately 2.25 seconds, required 35,463 samples and has a raw storage requirement of approximately 70 kB (kilobytes).

Figure 11:
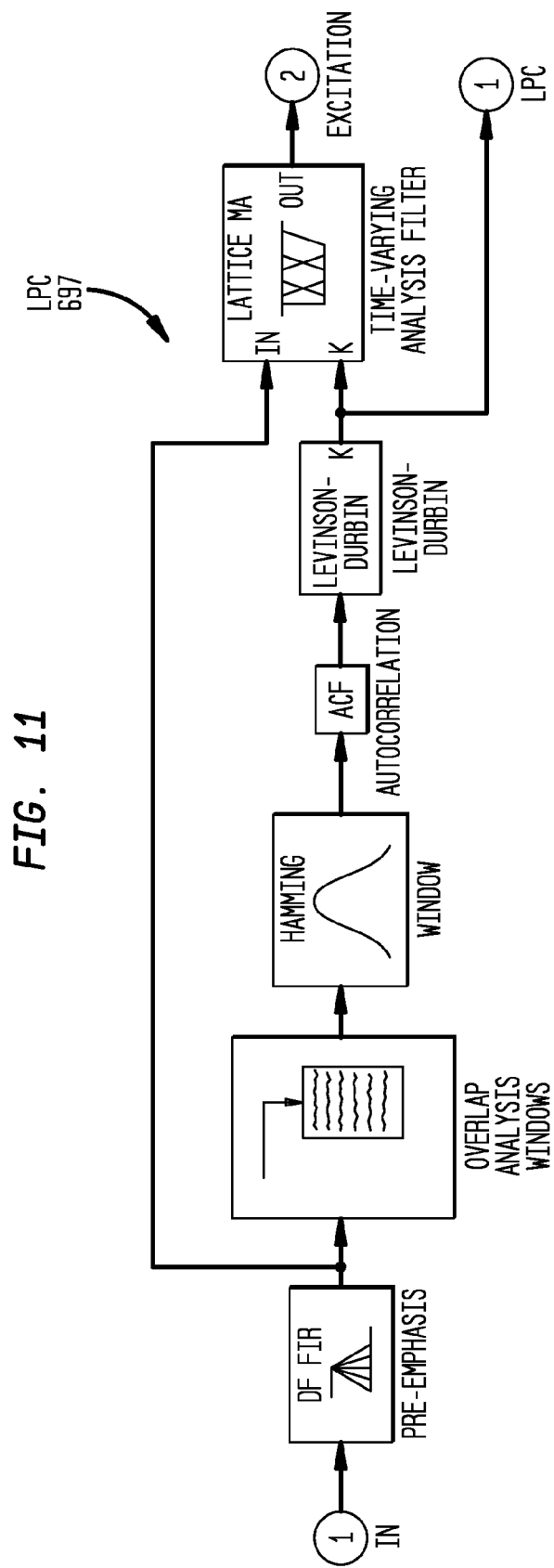
FIG. 11 is a signal flow diagram of the analysis part of a typical Linear Predictive Coder (LPC)

In FIG. 11 is shown a signal flow diagram of the analysis part of a typical Linear Predictive Coder (LPC) 697. This coder is based on Levension-Durbin recursion, and is well described in the literature. The analysis part of this type of LPC is used to derive a compressed representation of a speech signal, by expressing the signal in terms of a set of filter coefficients and an excitation signal to match these coefficients. The excitation signal is also known as a residual.

The analysis part of this type of LPC would typically be implemented in the fitting software for the hearing instrument system, or used during development to pre-calculate the compressed representation for each speech message and language required. The pre-calculated representation could then be provided as stored data in either the fitting software for downloading into the hearing instrument at fitting time, or if space permits, entirely within the hearing instrument during manufacture.

Figure 12:
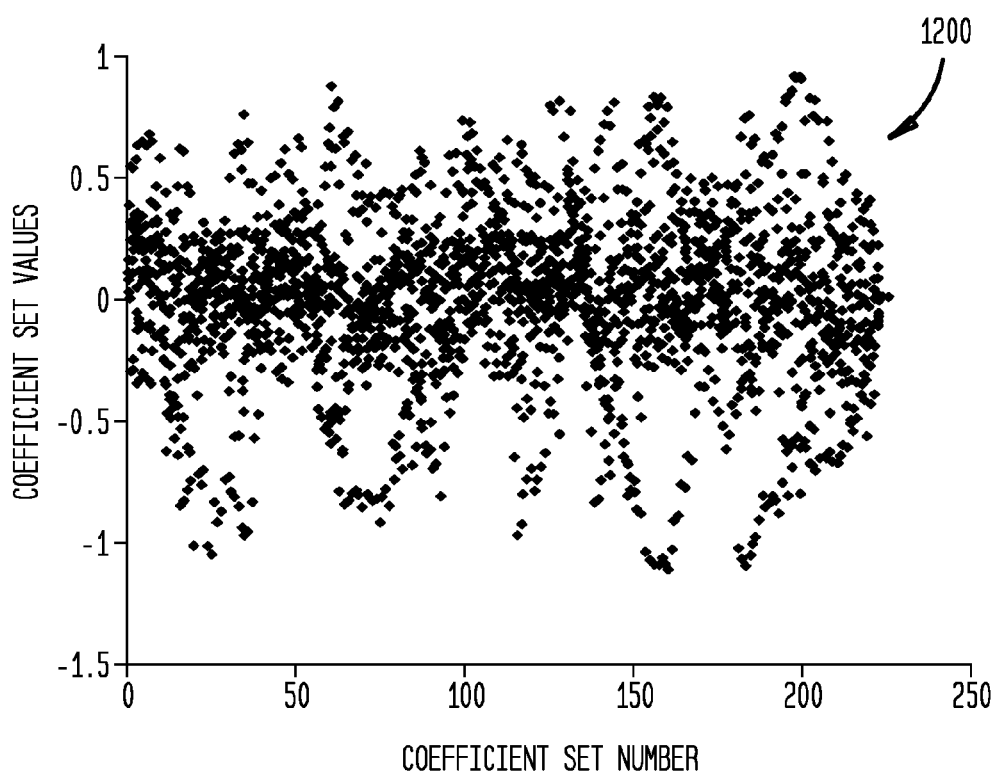
FIG. 12 is a calculated LPC coefficients for the segment of speech shown in FIG. 4.
Figure 14:
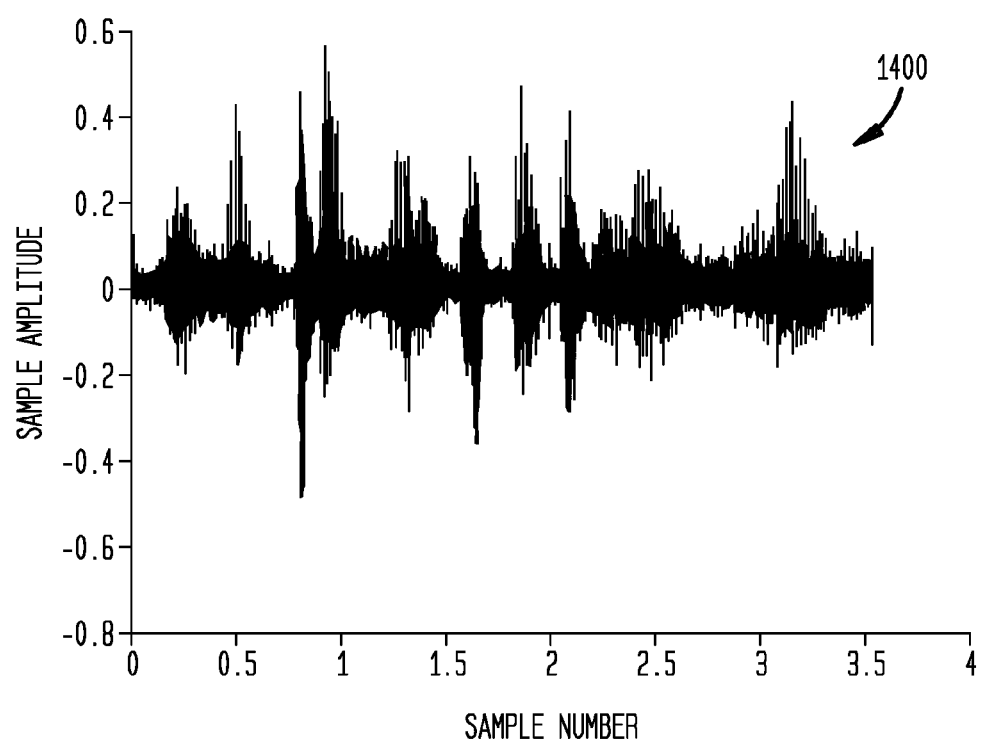
FIG. 14 is the calculated excitation signal for the segment of speech shown in FIG. 4.

The coefficients and excitation signal are derived for small segments of the speech signal being analysed, typically 20 milliseconds in length and overlapping by 10 milliseconds, such that together the entire speech message is represented by concatenated analysis segments. A signal flow diagram shown in FIG. 11 gives an example implementation of this method. The output from the analysis stage therefore consists of multiple sets of filter coefficients corresponding to each segment of the speech having been analyzed, and corresponding excitation signal of length in number of samples similar to the original signal. FIGS. 12 and 14 show examples of the calculated multiple coefficient sets 1200 and corresponding excitation signal 1500 respectively for the segment of speech "You have 10 minutes battery life remaining".

Figure 13:
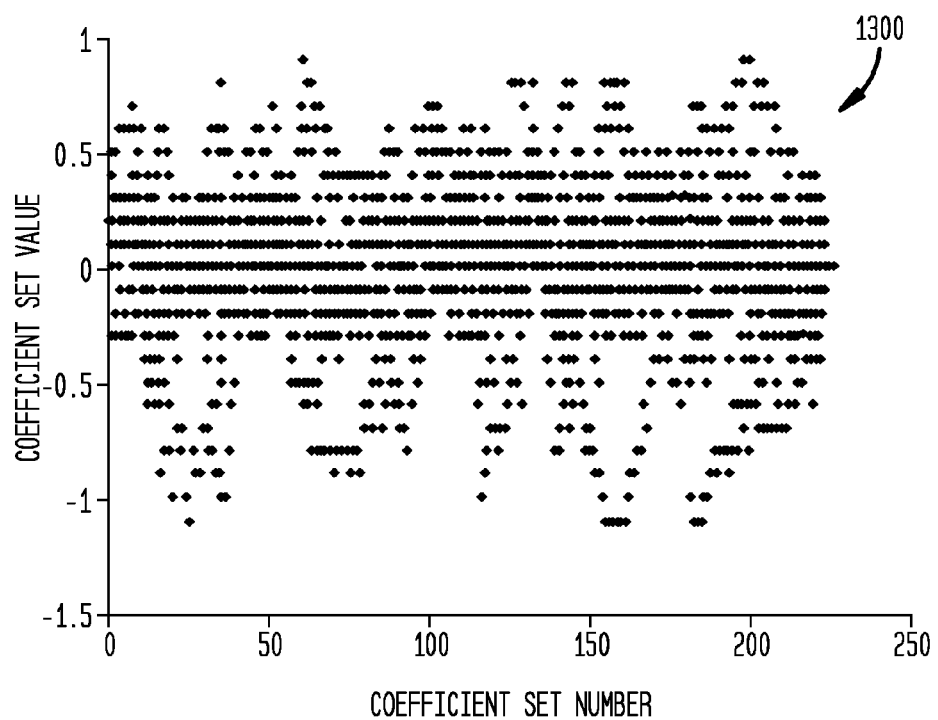
FIG. 13 is the 5 bit quantised LPC coefficients for the segment of speech shown in FIG. 4.
Figure 15:
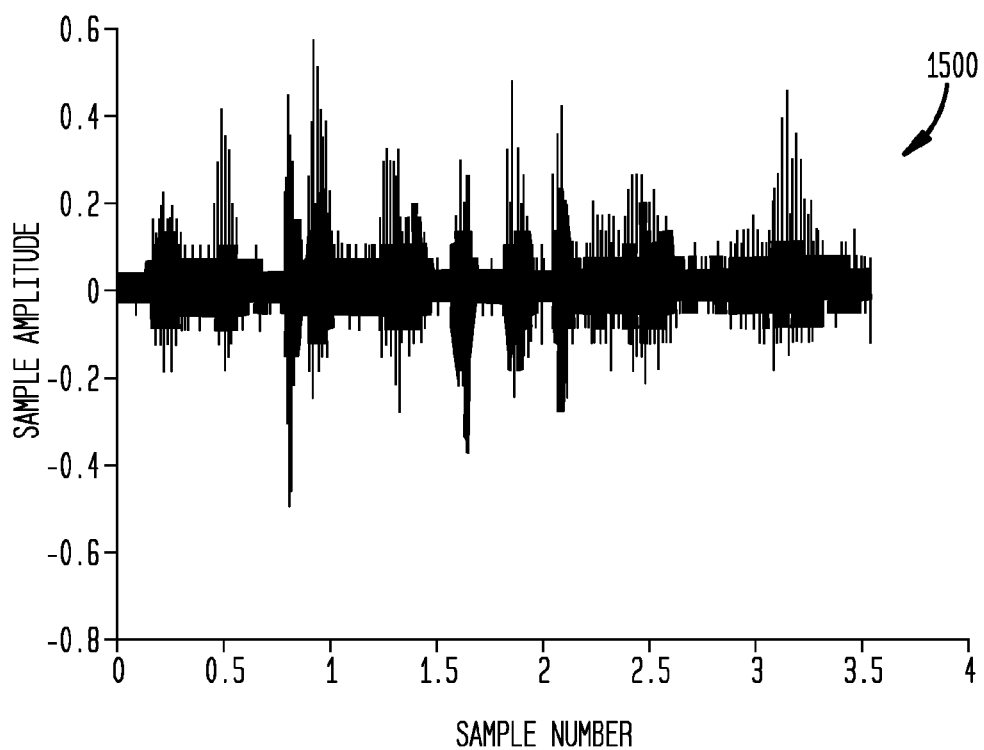
FIG. 15 is the 6 quantised excitation signal for the segment of speech shown in FIG. 4.

The coefficients and excitation signal are typically then quantized for efficient storage by 5 bits 1300 and 6 bits 1500 respectively, as shown in FIGS. 13 and 15. For the segment of speech "You have 10 minutes battery life remaining", the storage requirement is approximately 30 kB (kilobytes), a saving of close to 2.5 times the raw data requirement for the same speech segment.

Figure 16:
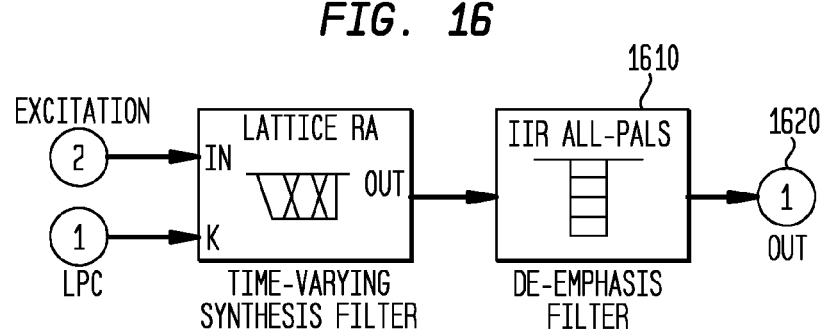
FIG. 16 is a signal flow diagram of the synthesis part of the example LPC.
Figure 17:
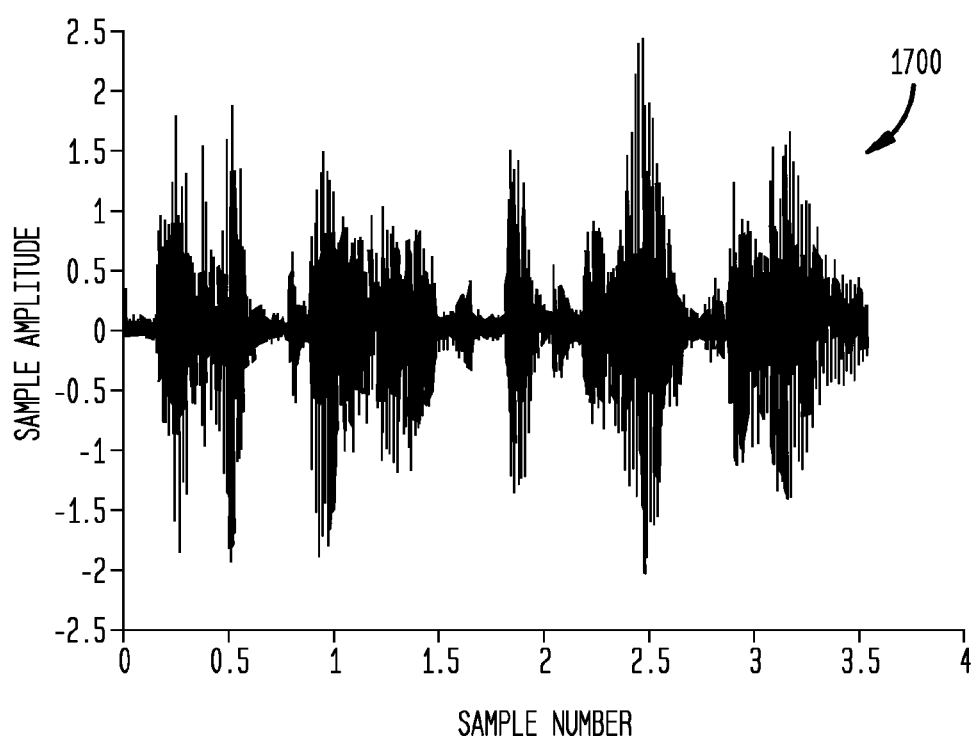
FIG. 17 is the reconstructed LPC for the segment of speech shown in FIG. 4.

In FIG. 16 is shown a signal flow diagram of the synthesis part of the example Linear Predictive Coder (LPC). The synthesis part is responsible for reconstructing an approximation of the original speech signal using the coefficient sets and excitation signal provided by the analysis part of the LPC. The synthesis part is required to be implemented in the hearing instrument in order to decompress the speech messages on the fly, as required. LPC Synthesis operates by applying each coefficient set in turn to an all pole IIR filter 1610 for each equivalent synthesis window, and applying the excitation signal as input to the IIR filter. The output 1620 of the IIR filter 1610 is the decompressed speech message for use as input to the signal path of the speech processor as required. FIG. 14 shows and example of the IIR filter 1610 output for the segment of speech "You have 10 minutes battery life remaining". The similarity to FIG. 10 will be recognized.

A further alternative implementation is to sample and store the speech messages as 8 kHz, 16 bit sampled data, and then interpolate up to the required playback sample rate of 16 kHz for example on playback.

A further alternative implementation is to store the speech messages as stimulation data, which has already been pre-processed through the recipient's map settings, or a portion of them. The pre-processing in order to provide the data in this format could be accomplished either during the detailed design of the product for all possible map settings, or at fitting time with the appropriate function implemented in the clinical software. In either case, only the required data is downloaded into the speech processor during fitting. This has the advantage that the behaviour of the signal path may be no longer important (or at least less so), as for example the data may be played directly out the speech processor, via the Data Encoder Formatter (DEF). The data size of the speech segments may also be more optimal at this point. FIG. 4 illustrates an implementation using the point of the signal path before the DEF 470, 570, 670, 770, 870. 970. In this case, the required message data simply replaces the normal signal stream for the period of time required. Similarly, the speech signal could be provided by using a signal appropriate for another part of the signal path, and inserting that signal. These approaches need to be carefully integrated with the signal processing system, so as to not interfere with, for example, any feedback controlled level or signal priority mechanisms which may affect subsequent processing.

One example of how safe operation might be achieved is given below in a further elaboration of the pseudo code presented above. When a speech message notification is required, the state of the speech processor should be checked and modified to be suitable first.

```
If (Notifiction = True)                    % There is an alarm condition
    % Setup the signal path for the sound message:
    Call SignalPathController(AGC=Off, ASC=Off);
    Call SignalPathController(MicrophoneSignal = Off);
    % Check what adaptive processes are running:
    If (ChannelGainsStable = False)
        Call StopChannelGain Adaptation;       % Pause adaptation
        ChannelGainsStopped = True;
    end if;
    If (VoiceActivityDetector = True)
        Call StopVoiceActivityDetector;        % Pause detector
        VoiceActivityDetectorStopped = True;
    end if;
    Alarm = IdentifyAlarm( );                  % Find out which alarm
    Select Case (Alarm)                        % Decide which message
    Case BattEmpty:
        CallPlayMessage(BATT_EMPTY_MESSAGE);
    Case BattLow:
        CallPlayMessage(BATT_LOW_MESSAGE)
    End Case;
    % Return the adaptive processes to how they were before
    If (ChannelGainsStopped = True)
        Call ReStartChannelGainAdaptation;%Restart adaptation
    end if;
    If (VoiceActivityDetectorStopped = True)
        Call ReStartVoiceActivityDetector;     % Restart
                                                 detector
    end if;
    % Return the signal path to how it was before
    Call SignalPathController(AGC=On, ASC=On);
    Call SignalPathController(MicrophoneSignal = On);
    Return;
```

Figure 8:
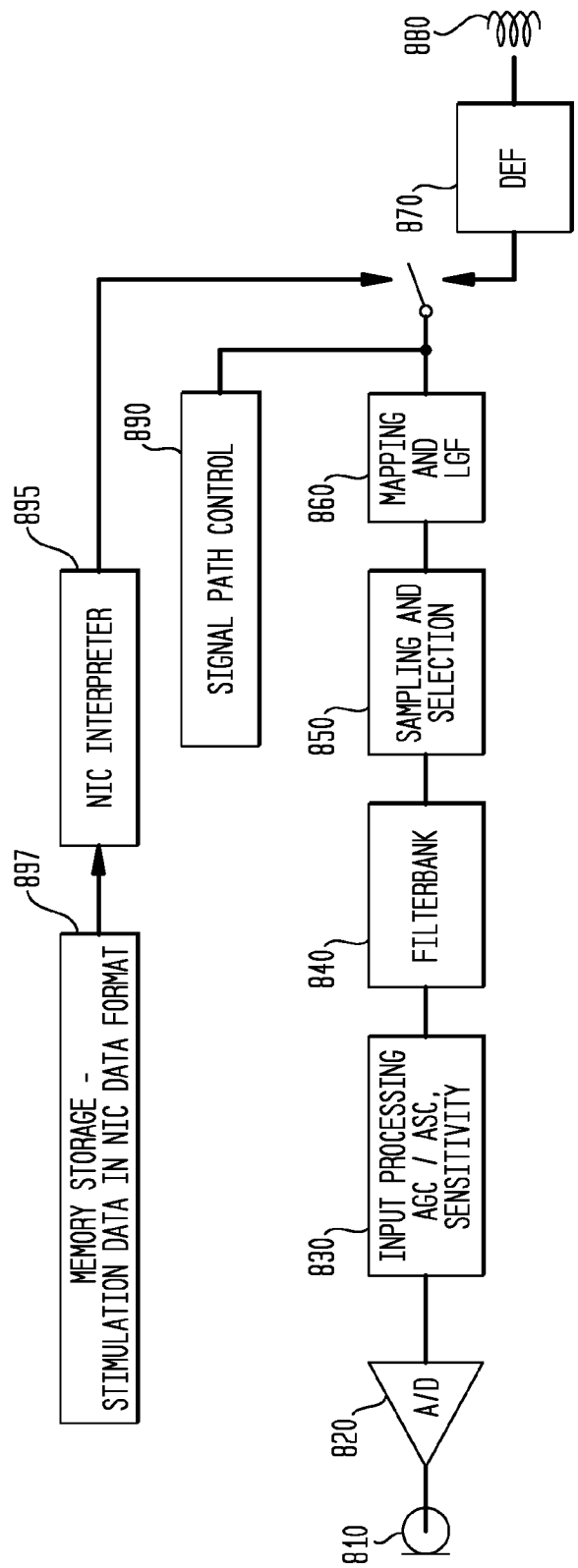
FIG. 8 is a block diagram illustrating another embodiment of this aspect of the present invention for a cochlear implant.

A further example would be to store the speech samples as stimulation data in NIC format, as described in the present applicant's co-pending PCT application, published as WO 02/054991, which is hereby incorporated by reference herein in its entirety. This has the advantage that the NIC format is also compact (since it incorporates loops for example) and the NIC tools are convenient and very flexible to use. Implementation using this format would require an NIC interpreter 895 in order to decode the NIC format data 897, as shown in FIG. 8.

It will be appreciated that the present invention is not limited to any specific mechanism for providing speech input to the prosthesis. For example, although not presently preferred, the speech signal could be generated in principle via a speech synthesizer, rather than stored files. Functionally, what is required is that the speech message is generated in response to an indication by the sound processor or prosthesis that a system level communication is required, and that this is provided using an input to the existing signal pathway for providing stimulus signals to the recipient.

The language spoken by the sound processor can be chosen at fitting time in the clinic, where the clinician would use programming software to choose which set of speech samples to download into the device.

The playback of speech messages is not limited to warnings of events. It can be used to construct an elaborate menu system which would otherwise be impossible to implement without many more buttons or displays. For example, the processor could prompt 'push the program button to test your microphones'.

Any discussion of documents, acts, materials, devices, articles or the like which has been included in the present specification is solely for the purpose of providing a context for the present invention. It is not to be taken as an admission that any of these matters form part of the prior art or were common general knowledge in the field relevant to the present invention as it existed before the priority date of each claim of this application.

What is claimed is:

1. A hearing prosthesis for delivering stimuli to a hearing-impaired recipient, comprising:
   a sound transducer for converting received sound signals into electric audio signals;
   a sound processor for converting said electric audio signals into stimuli signals;
   a stimulator for delivering said stimuli signals to the recipient;
   a memory for storing data representative of said received sound signals; and
   a controller configured to cause selected sound data to be retrieved from said memory and processed by said sound processor.

2. The hearing prosthesis of claim 1, wherein said stored data is in a form of electric audio signals which said processor, upon retrieval, converts into stimuli signals.

3. The hearing prosthesis of claim 1, wherein said stored data is in a form of partially or fully processed stimuli signals.

4. The hearing prosthesis of claim 1, further including a user interface for allowing a user to select data stored in said memory and trigger said controller to cause said selected data stored in said memory to be retrieved.

5. The hearing prosthesis of claim 1, wherein said hearing prosthesis is arranged to detect the presence of a signal with predetermined characteristics, corresponding to data stored in said memory; wherein, upon detecting a presence of a predetermined signal, said controller is triggered to cause said corresponding data to be retrieved.

6. The hearing prosthesis of claim 5, wherein said corresponding data represents a voice message describing the predetermined signal or a systematic pattern of stimuli that is recognizable to the user.

7. The hearing prosthesis of claim 1, wherein said controller is adapted to cause data, representative of an electric audio signal output from said sound transducer, to be stored in said memory.

8. The hearing prosthesis of claim 7, wherein a user interface allows said user to actuate said controller into causing said data to be stored.

9. The hearing prosthesis of claim 1, wherein said controller, upon being triggered, partially or fully inhibits delivery of other data to the stimulator while said selected data is being retrieved and conveyed to the user.

10. The hearing prosthesis of claim 1, wherein, when said selected data is previously delivered sounds signals, said signals are processed in an alternative manner to those originally conveyed to a user.

11. The hearing prosthesis of claim 1, wherein said stimulator receives stimuli signals wirelessly from said processor.

12. A method for delivering stimuli to a hearing-impaired recipient, via a cochlear implant, comprising:
converting received sound signals into electric audio signals;
converting said electric audio signals into stimuli signals;
delivering said stimuli signals to the recipient via an implanted electrode array;
storing data representative of said received sound signals;
retrieving a selected portion of sound data from a memory; and
processing said retrieval sound data by said sound processor.

13. The method of claim 12, further comprising:
receiving a user input selecting said sound data stored in said memory.

* * * * *